United States Patent
Georgeson et al.

(10) Patent No.: US 9,285,296 B2
(45) Date of Patent: Mar. 15, 2016

(54) SYSTEMS AND METHODS FOR STAND-OFF INSPECTION OF AIRCRAFT STRUCTURES

(71) Applicant: The Boeing Company, Seal Beach, CA (US)

(72) Inventors: Gary E. Georgeson, Tacoma, WA (US); James J. Troy, Issaquah, WA (US); Scott W. Lea, Renton, WA (US)

(73) Assignee: The Boeing Company, Chicago, IL (US)

( * ) Notice: Subject to any disclaimer, the term of this patent is extended or adjusted under 35 U.S.C. 154(b) by 518 days.

(21) Appl. No.: 13/732,789

(22) Filed: Jan. 2, 2013

(65) Prior Publication Data

US 2014/0184786 A1 Jul. 3, 2014

(51) Int. Cl.
*G01M 99/00* (2011.01)
*G01N 21/88* (2006.01)
*G01N 21/84* (2006.01)

(52) U.S. Cl.
CPC ............ *G01M 99/00* (2013.01); *G01N 21/8422* (2013.01); *G01N 21/8851* (2013.01); *G01N 2021/8867* (2013.01)

(58) Field of Classification Search
CPC ................................................. G01N 21/8851
USPC ........................................................ 348/128
See application file for complete search history.

(56) References Cited

U.S. PATENT DOCUMENTS

| 4,628,402 | A | 12/1986 | Covey |
| 6,433,867 | B1 * | 8/2002 | Esquivel ..................... 356/237.2 |
| 7,859,655 | B2 | 12/2010 | Troy et al. |
| 8,044,991 | B2 | 10/2011 | Lea et al. |
| 8,249,832 | B2 | 8/2012 | Motzer et al. |
| 2007/0113690 | A1 * | 5/2007 | Wilcox et al. ................ 73/865.9 |
| 2012/0320372 | A1 * | 12/2012 | Troy et al. .................. 356/237.2 |
| 2012/0327187 | A1 | 12/2012 | Troy et al. |
| 2013/0024067 | A1 | 1/2013 | Troy et al. |

* cited by examiner

*Primary Examiner* — Dave Czekaj
*Assistant Examiner* — Berteau Joisil
(74) *Attorney, Agent, or Firm* — Ostrager Chong Flaherty & Broitman P.C.

(57) ABSTRACT

A system for stand-off inspection comprising local positioning system hardware and a nondestructive evaluation instrument supported by a pan-tilt mechanism. The system further comprises a computer system that is programmed to perform the following operations: (a) directing the local positioning system hardware toward an area of a surface on a target object by control of the pan-tilt mechanism; (b) activating the local positioning system hardware to acquire an image; (c) processing the image to determine whether an anomaly is present in the area; (d) if an anomaly is present, determining coordinates of a position of the anomaly in a coordinate system of the target object; and (e) directing the nondestructive evaluation instrument toward a position corresponding to the coordinates. Optionally, the computer system is further programmed to measure one or more characteristics of the anomaly.

26 Claims, 9 Drawing Sheets

SYSTEMS AND METHODS FOR STAND-OFF INSPECTION OF AIRCRAFT STRUCTURES

BACKGROUND

This disclosure generally relates to automated systems and methods for stand-off inspection of structures, such as aircraft components. In particular, this disclosure relates to automated methods and systems for locating visible differences on a structural component from a distance and accurately measuring the locations of potential damage relative to a coordinate system of the inspected structure.

Finding and accurately measuring the locations of potential damage on a structure, such as a large commercial airplane, can be a laborious task. An efficient and automated process for addressing this problem would be valuable to many organizations involved in building and maintaining large vehicles and structures.

From two-dimensional images alone, it is difficult to get accurate measurements of aircraft locations defined in aircraft coordinates. Often, an item of known dimensions (like a tape measure) is inserted in the picture to give the analyst a size reference. But even with a reference scale, it can be difficult to measure a precise position in the desired coordinate system. Determining the correct location is especially difficult in areas where few uniquely identifiable landmark features exist. In addition, human analysis of a large number of potential damage areas would likely be error prone. Therefore, it would be desirable to have as much of the damage detection and localization process as automated as possible. Moreover, the entire process should be capable of being performed from a distance, without the need for any of the inspection or positioning equipment to contact the structure being inspected.

One specific problem in automated inspection is to provide a system and a method for automated inspection of dielectric tops on an aircraft wing. A dielectric top is a barrier dielectric patch which covers the head of a fastener to prevent lightning strikes from penetrating the structure and entering the fuel tank area. It is known that dielectric tops are susceptible to cracking after a certain number of years in service. An operator of aircraft so equipped tries to identify cracked dielectric tops in an accurate and fast manner, and then measure the depth of those cracks in an accurate and fast manner. Cracks above a certain length may require repair or replacement of the dielectric tops.

The existing solution for dielectric top inspection is a completely manual visual inspection and repair. Cracks greater than 0.1" in length are not allowed. Inspecting for these cracks will impact the service readiness of the airplane. Moreover, a typical airplane has about 18,000 dielectric tops.

It would be desirable to combine a stand-off local positioning system with a stand-off nondestructive evaluation (NDE) method to replace inspector's manual labor, increase the inspection rate, and find much smaller cracks than what can be seen visually, without physically touching the aircraft. To speed up an inspection, multiple stand-off NDEs could be run concurrently if multiple local positioning systems were available.

More generally, there is a need for stand-off NDE combined with a local positioning system that provides locating capability in a local (e.g., aircraft) coordinate system. An in-service NDE involving the capability to scan an aircraft structure without having to touch it, while obtaining all the location information without touching it, and to do so concurrently, would be very advantageous.

SUMMARY

The subject matter disclosed herein is directed to systems and methods which combine stand-off local positioning and stand-off NDE. More specifically, the systems described hereinafter provide for simultaneous and autonomous stand-off inspection locating, stand-off NDE, NDE measurement data mapping/correlation to a three-dimensional structure, and data storage and retrieval capability. The system combines the capabilities of a local positioning system with any one of a group of NDE hardware that can be used at a distance from the structure under inspection.

For the purpose of illustration, systems will be described hereinafter with reference to a particular application, namely, the standoff inspection of arrays of dielectric tops on aircraft wings. The particular embodiments disclosed hereinafter are designed to locate, inspect, and document cracked dielectric tops, indicate the appropriate disposition (no action required, monitor crack state (i.e., leave as is), quick repair, full repair). If needed, the same or a separate stand-off NDE can perform a quality inspection. A repair and subsequent inspection can be documented in a database that is remotely accessed by this system for later retrieval during future damage assessment and other maintenance operations.

The particular systems disclosed hereinafter provide a very rapid discrimination of cracked and non-cracked dielectric tops using a local positioning system to locate all specified dielectric tops and indicate those tops that call for further inspection; in addition it provides automated NDE options for measuring the depth of the cracks in those dielectric tops. The results of the crack measurements are saved in a remote database and autonomous repairs of various levels are initiated based upon the results. Repair or removal of cracked tops is done separately.

The means and methods disclosed hereinafter for implementing the combination of local positioning with stand-off NDE is not limited in its application to detecting cracks in dielectric tops. Other aircraft components can also be inspected using the techniques disclosed herein. More generally, the disclosed techniques have application in any situation where stand-off inspection of a structure is called for.

Some anomalies might be single points, in which case the system will record the position coordinates of the anomaly. When the anomaly is something bigger, like a crack or an area, additional location data can be recorded. In order to describe a crack, one can define a vector from a starting point to an ending point (which would be two points), or a multi-segment line which would be made of multiple points. In these cases, the system records sets of position coordinates corresponding to the set of two or more points. But when the anomaly becomes an area, then a more complex definition of the region is used. In this case, both position data and orientation data are recorded to define where it is located.

One aspect of the subject matter disclosed hereinafter is a system comprising local positioning system hardware, a NDE instrument, and a computer system programmed to execute the following operations: (a) controlling the local positioning system hardware to determine a direction vector to the target object and acquire image data representing an image of an area on a surface of the target object which is intersected by the direction vector; (b) processing the image data to determine whether the image of the area includes information indicating the presence of an anomaly in the area; (c) if it is determined in operation (b) that the image data includes information indicating the presence of an anomaly in the area, determining coordinates of a position of the anomaly relative to the coordinate system of the target object; (d) directing the NDE instrument toward an area on the target object having the recorded coordinates; and (e) controlling the NDE instrument to acquire NDE measurement data representing a characteristic of the anomaly using a stand-off NDE technique. The computer system may be further programmed to process the NDE measurement data to determine a value for the anomaly characteristic. In accordance with a further option, the local positioning system hardware comprises a video camera, a laser range meter, and a motion controlled pan-tilt unit that provides position measurement data for use in estimating the location of the video camera relative to the target object.

Another aspect is a system for stand-off inspection comprising a video camera, a laser range meter and a NDE instrument, all supported by a motion-controlled pan-tilt mechanism. The system further comprises a computer system is programmed to perform the following operations: controlling said video camera, said laser range meter and said motion-controlled pan-tilt mechanism to determine a direction vector to the target object, and acquire image data representing an image of an area on a surface of the target object which is intersected by the direction vector; processing the image to determine whether an anomaly is present in the area; if an anomaly is present, determining coordinates of a position of the anomaly in a coordinate system of the target object; and directing the NDE instrument toward an area on the target object corresponding to the coordinates. Optionally, the computer system is further programmed to measure a characteristic of the anomaly (e.g., the depth of a crack).

Yet another aspect is a method for NDE inspection of an area on a surface of a target object, comprising: determining, relative to a coordinate system associated with a target object, coordinates of a position for a visibly detectable anomaly (i.e. difference from nominal) on a surface of a target object using a local positioning system; directing a NDE instrument toward the visibly detectable anomaly using the recorded coordinates; acquiring measurement data representing a characteristic of the visibly detectable anomaly using the NDE instrument; and processing the measurement data to determine a value for the characteristic of the visibly detectable anomaly.

In accordance with a further aspect, a method for detecting and determining a position of a visible anomaly on a target object can be provided, said method comprising: (a) locating, by position and orientation, a local positioning system with respect to a target object; (b) determining an offset between the position and orientation of the local positioning system and a prior position and orientation of a local positioning system previously utilized to collect a set of reference images of the target object, the prior position and orientation being in the coordinate system of the target object; (c) relocating, by position and orientation, the local positioning system with respect to the target object in accordance with the offset determined in step (b); (d) acquiring a set of images of the target object from the position and orientation of the relocated local positioning system; (e) comparing the set of images to corresponding images within the set of reference images to detect a difference between the acquired images and the corresponding reference images; (f) determining coordinates of a position of the detected difference in the coordinate system of the target object; (g) recording the coordinates of the position of the detected difference; and (h) directing a NDE instrument toward the detected difference using the recorded coordinates. Optionally, the method may further comprise: (i) acquiring measurement data representing a characteristic of the detected difference using a NDE technique; and (j) processing the measurement data to determine a value for the aforementioned characteristic of the detected difference.

Yet another aspect is a method for stand-off inspection can be provided which comprises: (a) acquiring position measurement data of an area on a surface of a target object relative to the coordinate system of the target object using a local positioning system; (b) acquiring image data representing the area; (c) processing the image data to determine whether the image data includes information indicating the presence of an anomaly in the area; (d) if it is determined in step (c) that the image data includes information indicating the presence of an anomaly in the area, determining coordinates of a position of the anomaly relative to the coordinate system of the target object; (e) recording the coordinates of the position of the anomaly; (e) directing a NDE instrument toward an area on the target object having the recorded coordinates; and (f) acquiring NDE measurement data representing a first characteristic of the anomaly using a stand-off NDE technique. Optionally, the method may further comprise processing the NDE measurement data to determine a value for the first characteristic of the anomaly and/or processing the image data to determine a value for a second characteristic of the anomaly. If the anomaly is a crack, the first measured characteristic can be a depth of the crack, and the second measured characteristic can be a length of the crack. Image analysis software can be used to determine the position of the anomaly relative to the coordinate system of the target object and then determine the second characteristic of the anomaly. In one application, the target object is an aircraft and the anomaly is damage to the aircraft, for example, cracks in dielectric tops on an aircraft wing. Preferably, the NDE technique is selected from the following group: near-infrared spectroscopy, terahertz imaging, microwave imaging, x-ray backscatter imaging, stand-off infrared thermography, laser shearography, laser ultrasonic testing and laser vibrometry. Optionally, the method may further comprise: (1) directing a laser beam toward the area on the target object having the recorded coordinates; or (2) receiving coordinate positions of features on the surface of the target object from a three-dimensional database of feature positions and then controlling a video camera to scan across the surface, stopping at each of the coordinate positions of the features.

Determining the dimensions of an anomaly on the surface of a target object uses information about the relative angle between that surface and the measurement instrument. In particular, three-dimensional localization software can be used to determine a position and an orientation of the video camera relative to the coordinate system of the target object.

Other aspects are disclosed in the detailed description that follows.

BRIEF DESCRIPTION OF THE DRAWINGS

Reference will hereinafter be made to the drawings in which similar elements in different drawings bear the same reference numerals.

DETAILED DESCRIPTION

Figure 1:
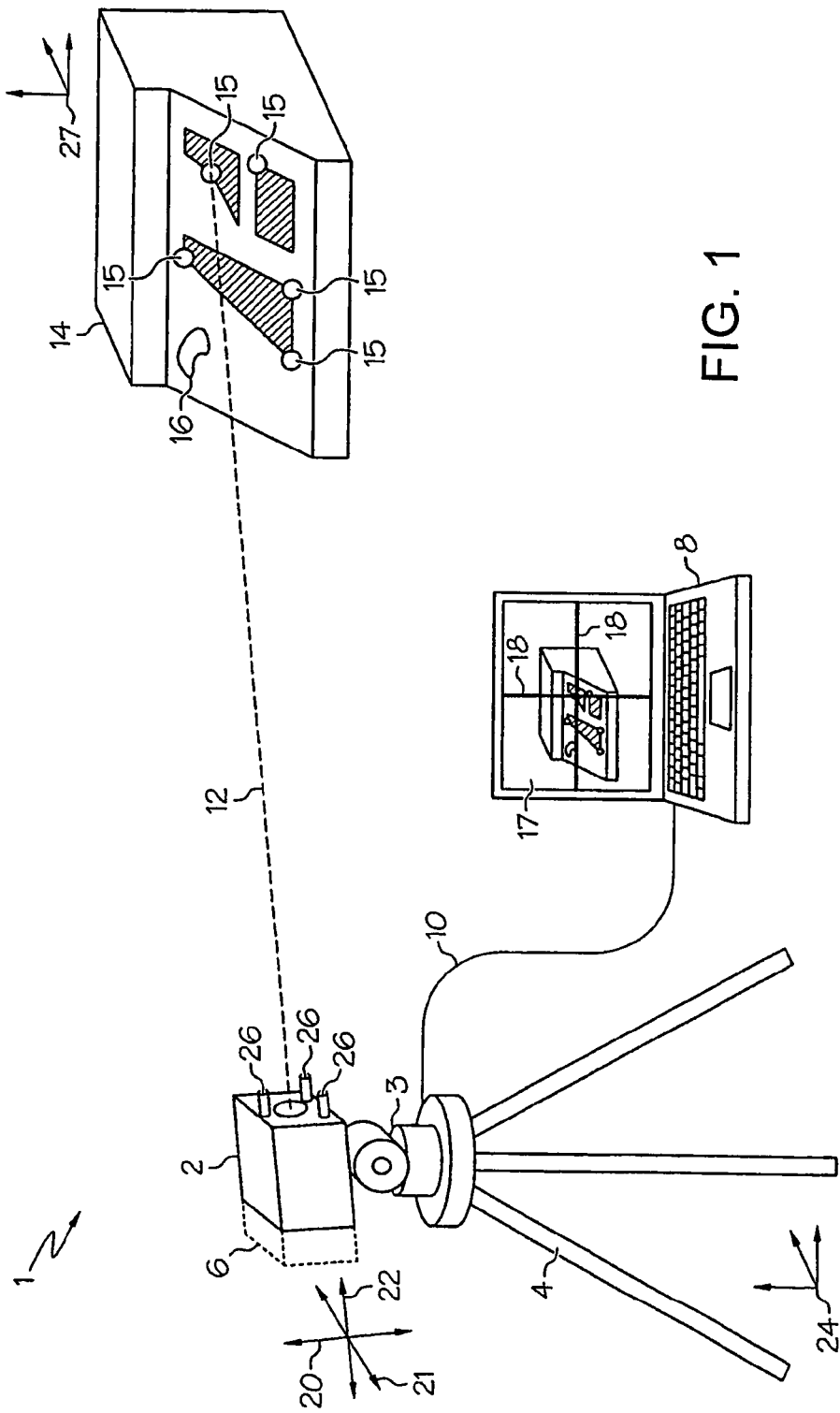
FIG. 1 is a diagram showing an isometric view of a local positioning system disclosed in U.S. Pat. No. 7,859,655.

FIG. 1 depicts one embodiment of a local positioning system 1 suitable for providing position data on a target object defined in the local coordinate system of the target object. The local positioning system 1 may comprise a video camera 2 having automated (remotely controlled) zoom capabilities. The video camera 2 may additionally include an integral crosshair generator to facilitate precise locating of a point within an optical image field display 17 for displaying video camera output on a personal computer or other display device 8. In applications in which the crosshair generator is not an integral component of the video camera 2, a crosshair generator 6 (shown in phantom) may be connected to the video camera 2 as a separate element for this purpose or overlaid on the video stream on the personal computer or display device 8.

The video camera 2 may be coupled to a motion-controlled pan-tilt mechanism 3 mounted on a tripod support 4 or an alternative support frame (e.g., a gantry). The motion-controlled pan-tilt mechanism 3 may be capable of positionally adjusting the video camera 2 to selected angles around the vertical, azimuth (pan) axis 20 and the horizontal, elevation (tilt) axis 21, as well as rotation of the video camera 2 to selected angles about a roll camera axis 22. For the implementation discussed here, measurement and control of the roll axis is not required.

A direction vector that describes the orientation of the camera relative to a fixed coordinate system 24 of the tripod 4 (or other platform on which the pan-tilt unit is attached) is determined from the azimuth and elevation angles, as well as the position of the center of crosshair marker in the optical field when the camera is aimed at a point of interest 16 on a target object 14. In FIG. 1, the direction vector is represented by line 12 which extends from the lens of camera 2 and intersects a location 15 on target object 14.

The video camera 2 and the pan-tilt mechanism 3 may be operated by a personal or other computer 8. The computer 8 may communicate with video camera 2 and pan-tilt mechanism 3 through a video/control cable 10. Alternatively, the computer 8 may communicate with video camera 2 and pan-tilt mechanism 3 through a wireless communication pathway (not shown). Alternatively, the computer may be integrated with the camera. Control of the pan-tilt mechanism 3 and therefore, the orientation of the video camera 2 may be controlled using the keyboard of computer 8, a mouse (not shown), a track ball (not shown) or another input device. The optical image field 17, with crosshair overlay 18, as sighted by the video camera 2, may be displayed on the monitor of computer 8.

Three-dimensional localization software may be loaded into computer 8. For example, the three-dimensional localization software may be of a type that uses multiple calibration points 15 at a distance on the target object 14 (such as a surface on an aircraft) to define the location (position and orientation) of video camera 2 relative to target object 14. In some applications, the three-dimensional localization software may utilize a minimum of three calibration points 15 on the target object 14, in combination with pan and tilt data from the pan-tilt mechanism 3, to define the relative position and orientation of the video camera 2 with respect to the local coordinate system 27 of the target object 14. The calibration points 15 may be visible features of known position in the local coordinate system 27 of the target object 14 as determined from a three-dimensional database of feature positions (e.g., a CAD model) or other measurement technique. The calibration points 15 may be used in coordination with the azimuth and elevation angles from the pan-tilt mechanism 3 to solve for the camera position and orientation relative to the target object 14.

Once the position and orientation of the video camera 2 with respect to the target object 14 have been determined, the computer 8 may be operated to rotate and zoom the optical image field of the video camera 2 to a desired location 16 of unknown position on the target object 14, which may be a damage/repair location on an aircraft, for example. At this position of the direction vector, the orientation of the video camera 2 (which may include the respective angles of the video camera 2 along the azimuth axis 20 and the elevation axis 21) may be recorded. By using the azimuth and elevation angles from the pan-tilt unit and the relative position and orientation of the camera determined in the calibration process, the location of the point of interest 16 can be determined relative to the coordinate system 27 of the target object 14. The damage/repair location 16 on the target object 14 may be sized by aligning the crosshairs 18 in the optical image field of the video camera 2 along the boundary of the damage/repair location. In the case of a crack, the length of the crack may be measured by moving the crosshairs from one tip of the crack to the other tip of the crack, traveling along the crack path.

The reverse process, in which the position of a point of interest 16 may be known in the target object's coordinate system (from a previous data acquisition session, a CAD model, or other measurement), can also be performed. In this situation, the camera may be placed in any location on the work area where calibration points are visible (which may be in a different location than the location where the original data was recorded) and the camera pose calibration step may be performed. The direction vector 12 from the point of interest to the camera 2 may be calculated in the target object's coordinate system 27. The inverse of the camera pose transformation matrix may be used to convert the direction vector into the coordinate system of the camera. The azimuth and elevation angles may then be calculated and used by the pan-tilt unit to aim the camera 2 at the point of interest on the target object 14.

In some applications, one or more laser pointers may be mounted on the camera 2 and aligned with the direction vector 12. In the embodiment depicted in FIG. 1, the camera 2 has three laser pointers 26 mounted thereon. The laser pointers 26 provide visual indications on the target object 14 as to the aim or direction of video camera 2. This sighting feature provided by laser pointers 26 may be helpful in aiding rapid selection of positional calibration points 15 and points of interest 16 on the target object 14, since the intersection of the laser beams (not shown) emitted from the laser pointers 26 with the target object 14 can be visible to the naked eye. Laser pointers can also be used when recalling points in the target object's coordinate system 27 (which could be previous repair locations or other points of interest) by showing the location on the target object 14.

In a typical implementation, the local positioning system instrument may be set up within about 10-50 feet of the target object 14. The target object 14 may, for example, be a surface of an aircraft that is equipped with an array of dielectric tops. The calibration points 15 on the target object 14 may be selected and used by the three-dimensional localization software loaded onto the computer 8 in conjunction with the pan and tilt data (i.e., azimuth and elevation angles) from the pan-tilt mechanism 3 to determine the position and orientation of the video camera 2 with respect to target object 14. The calibration points 15 may be feature points of known position in the local coordinate system 27 of the target object 14 as determined from a three-dimensional CAD model or other measurement technique. In some implementations, the pan-tilt unit 3 may be attached to a portable support, such as a tripod 4 or other mobile device. In other implementations, the pan-tilt unit could be attached to stationary support, such as the walls of an airplane hangar.

The three-dimensional localization software loaded onto the computer 8 may determine the position and orientation of the video camera 2 with respect to the target object 14 and generate a camera pose transformation matrix using one of three methods: (1) a vector-based approach; (2) position and orientation based on 5- or 7-point technique; and (3) a laser range-based system.

The vector-based approach may utilize three calibration points 15 on the target object 14 and solve simultaneous equations to determine the position of the video camera 2 with respect to the target object 14. This assumes the relative orientation of the camera is known.

The position and orientation calibration based on 5- or 7-point techniques may determine both the position (x, y, z) and the orientation (roll, pitch, yaw) of the video camera 2 relative to the target object 14 in the manner disclosed in U.S. Pat. No. 7,859,655 (the disclosure of which is incorporated herein in its entirety).

In alternate embodiments, an off-the-shelf laser-based distance measurement device (not shown) may be integrated into the system to create a laser hybrid system, which may be incorporated onto the pan-tilt mechanism 3 and which may use measurement data from the laser to obtain an estimate of the distance from video camera 2 to calibration points 15 on target object 14.

Once the position and orientation of the video camera 2 with respect to the target object 14 are determined and the camera pose transformation matrix generated, camera pan data (angle of rotation of video camera 2 about the azimuth axis 20) and tilt data (angle of rotation of video camera 2 with respect to the elevation axis 21) may be used in conjunction with the calculated position and orientation of video camera 2 to determine the (X,Y,Z) position of any point of interest (such as the damage/repair location on the skin of the aircraft) in the coordinate system of the target object 14. The video camera 2 may then be aimed at the damage/repair location on the target object 14, with the center and/or outline of the damage/repair location defined.

Because the position of the damage/repair location on the target object 14 may not initially be known, the pan and tilt angles of the pan-tilt mechanism 3 may be used to determine the direction vector 12 in the local camera coordinate system 24 of the video camera 2. Determination of the surface position of the damage/repair location may be made by any one of the following methods: (1) an approximation using the ray intersection from a polygonal surface formed from the calibration points, or other user-selected features of known position on the target object; (2) three-dimensional data from a CAD model, for example; or (3) the distance from the optional laser-based measurement device. At this stage, the camera pose transformation matrix may be used to transform or convert the damage/repair location, which is initially defined in the local coordinate system of video camera 2, into the local coordinate system of target object 14.

A three-dimensional model coordinate system and maintenance database of the target object 14 may then be accessed by computer 8 to locate previous locations of damage, repairs and/or other issues on the target object 14. Present repair of the damage/repair location on the target object 14 may then be planned and completed based on the positional and geometric relationships of the previous damage, repairs and/or issues with the damage/repair location. The positional and geometric information of the video camera 2 when its optical image field is aimed at the damage/repair location may be saved and superimposed on the three-dimensional model, which may be maintained in a database. Digital photographs of the damage/repair location may additionally be taken using the video camera 2 or other camera and saved in the database. Accordingly, the updated database is available in the event that a subsequent repair of the target object 14 is called for.

An image processing method may be used to estimate the three-dimensional position of an anomaly from an image captured by the camera of a local positioning instrument, but in order to determine the three-dimensional coordinates of the anomaly, the system must first determine the three-dimensional position of the center of the image. Assuming that the local positioning system is pointed at the proper location, those coordinates could be used as the center of the image along with a local positioning system calibration matrix. But a more robust solution is to use the laser range meter 638 to take a distance reading at the current position where it is pointed and then the local positioning system software uses that measurement, along with the pan and tilt angles to compute the current three-dimensional coordinates. The three-dimensional coordinates measured by the local positioning system are then used by an image processing method to derive the three-dimensional coordinates for the anomaly. Position measurement data acquired by the local positioning system (and its calibration matrix) is used along with data derived from the image to determine the length of the anomaly. (Data from the camera image alone or the local positioning system alone is not sufficient to determine position or length of the anomaly.)

Figure 2:
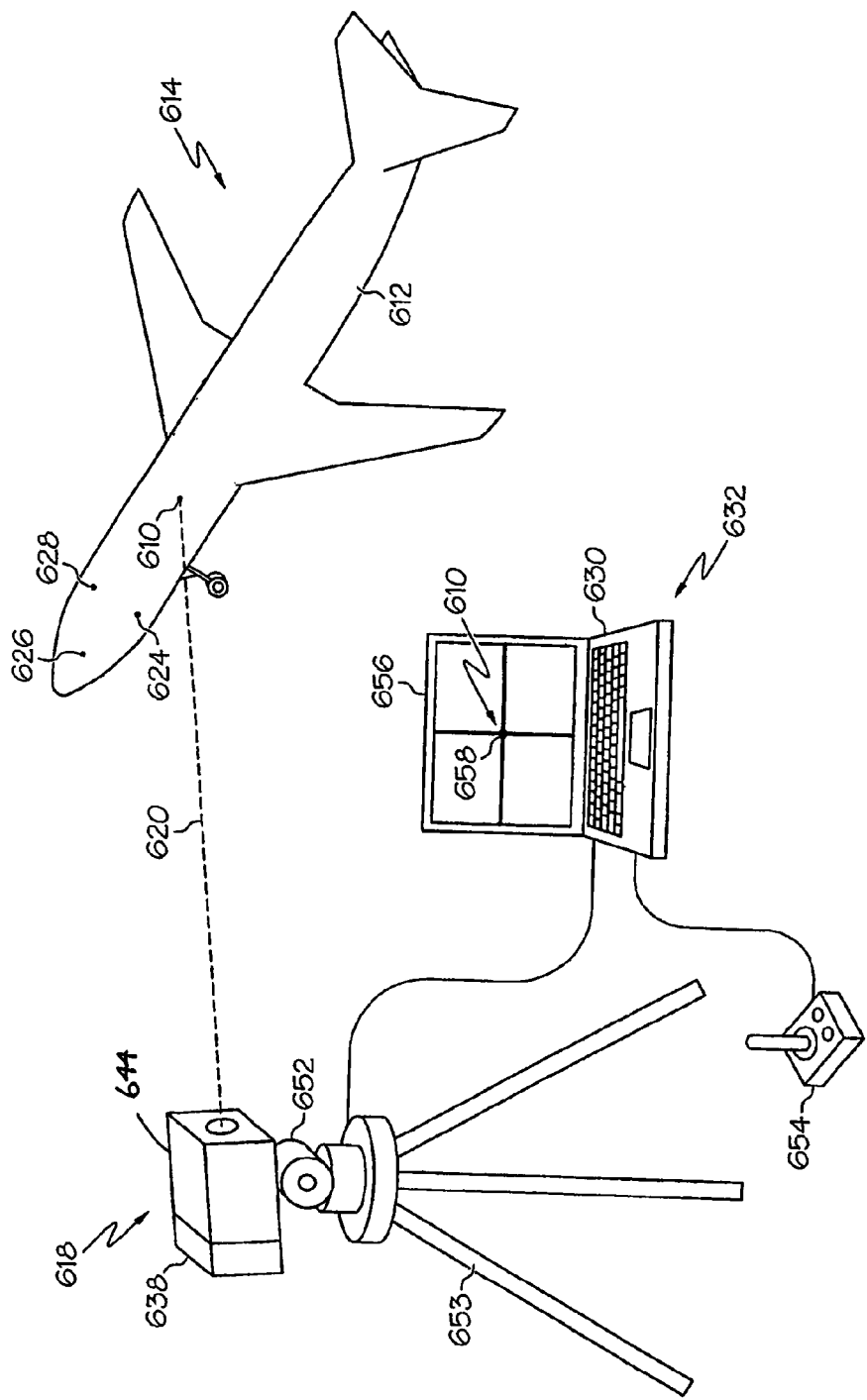
FIG. 2 is a diagram showing an isometric view of an alternative local positioning system disclosed in U.S. Pat. No. 7,859,655.

The embodiment shown in FIG. 2 can be used to determine a position of a point of interest 610 on a surface 612 of a target object 614 having a target object coordinate system using a pointing instrument 618 having an aim point axis 620 and having an instrument coordinate system. One method includes measuring an orientation of the aim point axis 620 in the instrument coordinate system when the aim point axis 620 of the instrument 618 is in turn aligned with each of three calibration points 624, 626 and 628 on the surface 612 of target object 614, wherein positions of the three calibration points 624, 626 and 628 in the target object coordinate system are known. This method also includes measuring a distance (i.e., range) substantially along the aim point axis 620 from the instrument 618 to each of the three calibration points 624, 626 and 628. This method also includes calculating a calibration matrix which transforms a position defined in the instrument coordinate system to a position defined in the target object coordinate system using at least the measured orientation and distance in the instrument coordinate system corresponding to the three calibration points 624, 626 and 628 and the known positions of the three calibration points 624, 626 and 628 in the target object coordinate system. This method also includes measuring an orientation of the aim point axis 620 in the instrument coordinate system when the aim point axis 620 of the instrument 618 is aligned with the point of interest 610. This method also includes calculating a position of the point of interest 610 in the target object coordinate system 616 using at least the measured orientation of the aim point axis 620 in the instrument coordinate system 622 corresponding to the point of interest 610, the calibration matrix, and at least one of a distance substantially along the aim point axis 620 from the instrument 618 to the point of interest 610 and a model of the surface 612 of target object 614 in the target object coordinate system. This method also includes storing the calculated position. In one variation, the stored calculated position is stored in computer memory 630 of a computer 632 which is operably coupled to the instrument 618 to at least receive signals corresponding to distance and orientation measurements of the aim point axis 620 of the instrument 618 in the instrument coordinate system and to perform the previously described operations to calculate the position of the point of interest 610 in the target object coordinate system.

In accordance with the embodiment shown in FIG. 2, the distance (range) substantially along the aim point axis 620 from the instrument 618 to the point of interest 610 is measured using a laser range finder 638), the position of the point of interest 610 defined in Cartesian coordinates in the instrument coordinate system 622 is calculated using forward kinematics of the instrument 618 and the measured pan and tilt angles 634 and 636 and distance corresponding to the point of interest 610 defined in spherical coordinates in the instrument coordinate system 622, and the calibration matrix is used to transform the position of the point of interest 610 defined in Cartesian coordinates in the instrument coordinate system 622 to the position of the point of interest 610 defined in Cartesian coordinates in the target object coordinate system 616.

In the embodiment shown in FIG. 2, the instrument 618 includes a pan-tilt unit 652 which is supported by a tripod 653. The instrument 618 is mounted on the pan-tilt unit 652 to allow the instrument 618 to be rotated in pan and tilt. In one variation, the instrument 618 comprises a video camera 644 equipped with a laser range finder 638, and the computer 632 includes a joy stick input device 654 and a monitor 656. In one modification, the computer 632 is programmed to control the pan-tilt unit 652 through the joy stick input device 654, to display a field of view of the video camera 644 on the monitor 656, to overlay a representation 658 (such as the center of cross-hairs) of the aim point axis 620 on the display, and to measure the pan and tilt angles (and distance for the calibration matrix) when a user of the joy stick input device 654 aligns the representation 658 of the aim point axis 620 on the display with the point of interest 610 on the display and indicates such alignment to the computer 632.

In addition, the local positioning system (LPS) shown in FIG. 2 is capable of automatically detecting visible anomalies (such as damage) on the surface of a target object (such as an aircraft), and then automatically measuring the locations and sizes of those anomalies in the local coordinate system of the target object. The video or other digital camera is used to collect a sequence of image pairs. Digital image processing software then performs an image change detection process in which the differences between two or more images are detected and the two-dimensional pixel locations in the image where those differences reside are determined. The two-dimensional data is then utilized to direct the local positioning system unit to take measurements and compute the three-dimensional positions of those areas of interest expressed in the coordinate system of the target object. To accomplish the above, the control method of the local positioning system is extended to automate the image collection, analysis, and conversion into three-dimensional target coordinates. Such processes are described in detail in U.S. patent application Ser. No. 12/897,408, which issued on Jun. 3, 2014 as U.S. Pat. No. 8,744,133 (the disclosure of which is incorporated by reference herein its entirety).

Several embodiments will be described hereinafter in terms of finding and measuring the locations of areas on an aircraft surface in which potential damage may have occurred. In one embodiment the damage is determined from a series of before-and-after image pairs, in which digital image processing software is utilized to determine whether any visible change has occurred over an interval of time between when a reference image was acquired and when an inspection image of the same region is acquired. Once potential image differences are found, the corresponding three-dimensional locations (X,Y,Z) on the aircraft are determined, preferably in the local coordinate system associated with the aircraft instead of a coordinate system defined in the hangar or measurement device reference frame. The local aircraft coordinate measurements are recorded or otherwise used to direct further detailed inspection, repairs, and/or generation of reports related to aircraft damage.

When triggered by a human operator, timer, or automated application, the system depicted in FIG. 2 can capture a sequence of images and compare them to a reference image set. (Alternatively, it may be possible to detect an anomaly without using a reference image.) Differences between pairs of images are detected and the image pixel locations are used to define the direction in which to point the video camera. When the desired location is reached, the system performs a distance measurement and computes the Cartesian coordinate (X,Y,Z) position on the surface defined in the coordinate system of the target object. This position data is then displayed, stored, or sent to the client application that requested the data.

For certain embodiments of the described process, the target object and local positioning instrument are in fixed positions relative to each other, but in some use cases the relative position may have changed. In these situations, if the positions and orientations of the camera in the before and after images are not too far apart, image processing techniques are used to estimate the offset. Techniques for image-based localization, such those used in Simultaneous Localization and Mapping (SLAM), may be used. In SLAM, relative displacements of features common to both images are used to provide the offset estimate. For this, relatively small position and orientation changes are used, along with substantial overlap between the images in order to achieve registration. Additionally, known reference dimensions are used to determine the scale of the displacement.

Using small position and orientation changes, along with a large amount of image overlap, is not always possible. A more general process is needed to ensure that the relative realignment between the target and instrument can be achieved for a wider range of conditions. One solution is to provide a way to move the instrument back into the same relative position and orientation as it was when the reference image was taken. As described above, one option is to put the local positioning instrument on a movable support, such as a mobile platform, robotic arm, or crane. After the local positioning unit has been calibrated in its current position relative to the target object (either of which may be different from the initial reference position), the offset transformation matrix can be computed. The mobile platform then translates and rotates the instrument by the offset amounts to achieve realignment with the original position and orientation. Any residual small differences can be compensated by image shifting/rotation based on image processing techniques similar to those used in image-based localization.

Figure 3:
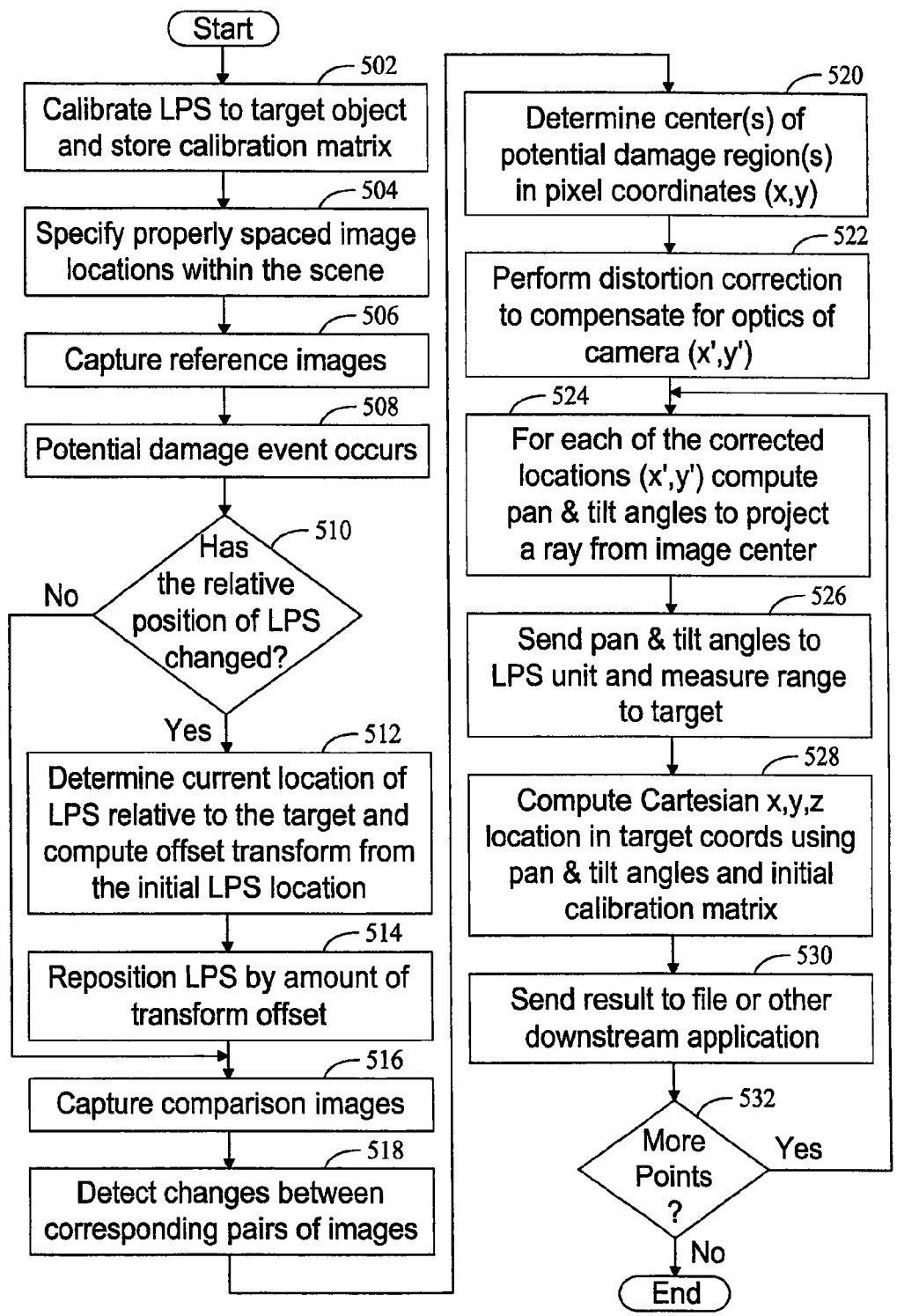
FIG. 3 is a flowchart showing a process for determining the locations of visible differences in reference and inspection images of a target object in accordance with one embodiment disclosed in U.S. patent application Ser. No. 12/897,408 (the disclosure of which is incorporated herein in its entirety).

FIG. 3 is a flowchart that illustrates the process for locating positions in three dimensions of visible differences on an object. More specifically, the flowchart provides details associated with the automated imaging capture, image processing, instrument realignment, and integration with the LPS three-dimensional measurement process.

In step 502, the LPS is calibrated to a target object and a calibration matrix is stored. Properly spaced image locations are specified within the scene associated with the target object (step 504). An initial set of images is captured (step 506). Specifically, a sequence of reference images are captured along with X,Y,Z location data associated with the image center for each of the images captured.

The target object, for example, an aircraft, is placed into service and over time, a potential damage event occurs (step 508) and the target object is once again placed in a position with respect to the LPS. In a typical scenario, the position of the object with respect to the LPS may be somewhat different than the relative position between the two when the initial images were captured, resulting in an affirmative response when considering whether the relative position of the LPS has changed in step 510.

In response to a determination (in step 510) that the relative position of the LPS has changed, the current location of the LPS relative to the target is determined and an offset transform from the initial LPS location is computed (step 512). The LPS is repositioned by the offset transform amount (step 514). After LPS repositioning (or if it was determined in step 510 that the relative position of the LPS has not changed), a sequence of current images are captured from the same relative location (step 516). Pairs of images taken from the same position and orientation are compared to detect changes (step 518). For example, regions of change can be determined using digital image processing techniques. One such process may involve image subtraction, blur filters, and image segmentation steps.

The locations of any differences are determined in step 520. The centroid of each area is found and converted into pixel coordinates (x, y). A distortion correction is performed (step 522) to compensate for the optics of the camera associated with the LPS, where two-dimensional image corrections are applied, resulting in (x', y'). This correction may depend on, for example, the lens optics, zoom, and focus levels. In accordance with one embodiment, the corrections are determined experimentally and recalled at run-time using a lookup table.

A target vector is determined in step 524, where the corrected pixel values (x', y'), along with the initial image location data, are used to determine new azimuth and elevation (pan and tilt) angles defining the vector from the LPS instrument to the target object. In this embodiment, the LPS includes a pan and tilt unit which is driven to the determined pan and tilt angles and a new range measurement is taken (step 526). The pan and tilt unit is similar to pan and tilt units used on such things as security cameras and telescopes and provides highly accurate data with respect to a positioning of one or both of the range measurement device and the imaging device.

A location is computed (step 528), for example, in Cartesian coordinates associated with the target object. These target coordinates are determined from the pan, tilt, and range data, along with the object-to-instrument calibration matrix. Resulting measurement data can be saved, displayed, or sent to other client applications through socket connections (step 530). A determination is then made (step 532) whether more points are to be transferred. If Yes, then the process resumes with pan and tilt calculations associated with the next location; otherwise the process ends.

One embodiment of a system for simultaneous and automated stand-off inspection locating, stand-off NDE, NDE measurement data mapping/correlation to a three-dimensional structure, and data storage and retrieval capability will now be described with reference to FIG. 4. The system combines the capabilities of a local positioning system 30 with an NDE instrument 32 that can be used at a distance from a structure under inspection. For the purpose of illustration, a system will be described with reference to a particular application, namely, the standoff inspection of arrays of dielectric tops 34 on an aircraft wing 36. However, the combined LPS/NDI system disclosed herein is not limited in its application to inspecting dielectric tops on an aircraft wing.

Figure 4:
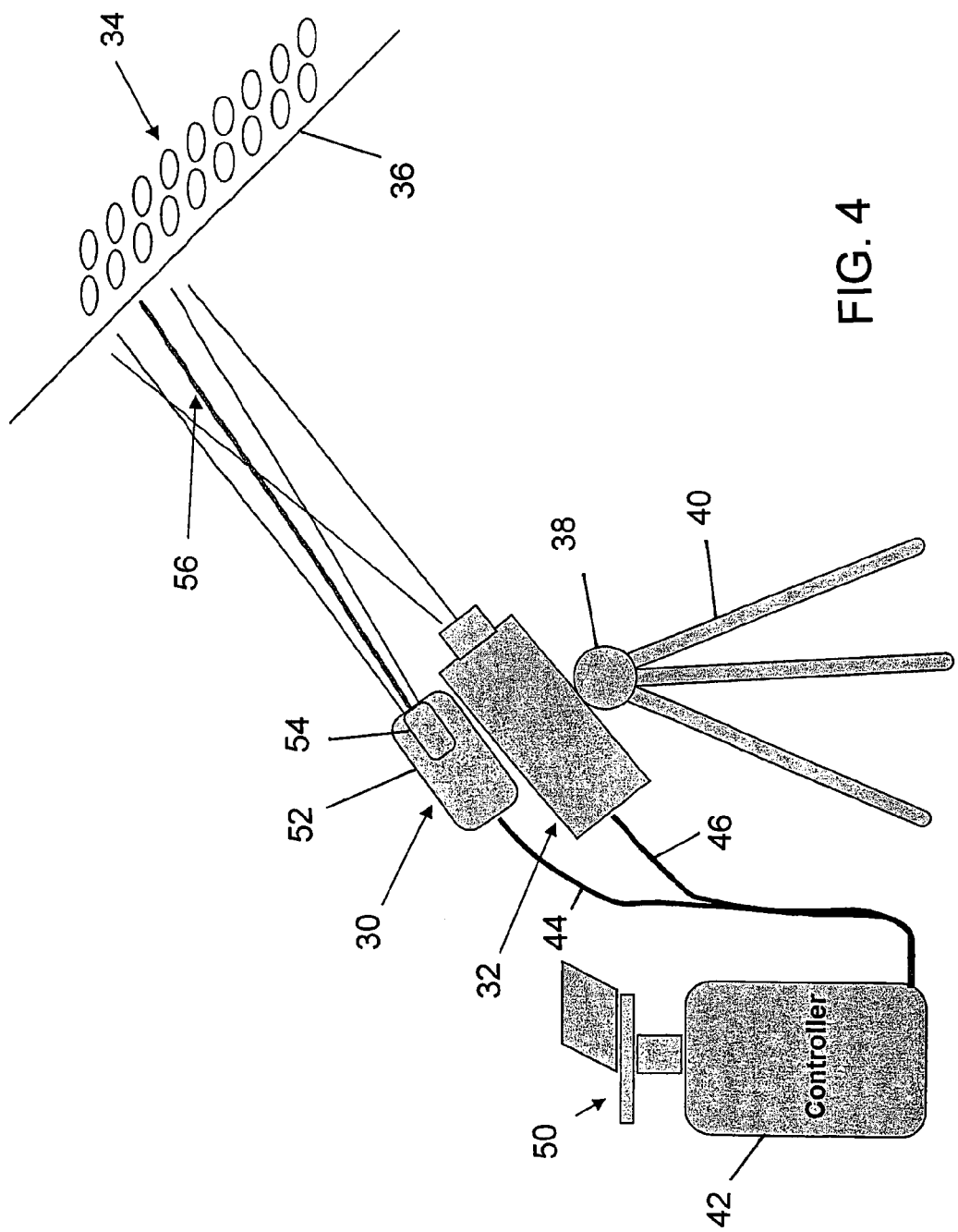
FIG. 4 is a diagram showing a system for stand-off inspection of an array of dielectric tops on an aircraft wing in accordance with one embodiment wherein the local positioning system and the NDE instrument are separate units.

In the embodiment shown in FIG. 4, the local positioning system 30 includes a pan-tilt mechanism 38, a video camera 52, a laser range meter 54, and a notebook or laptop computer 50. The system shown in FIG. 4 further comprises an NDE instrument 32, which is mounted on the pan-tilt mechanism 38. In this case the video camera 52 may be rigidly attached to the NDE instrument 32, which is mounted on the pan-tilt mechanism 38. (Alternatively, the video camera may be mounted on the pan-tilt mechanism, with the NDE instrument rigidly attached to the video camera.) The pan-tilt mechanism 38 can be mounted on a tripod 40 or other suitable support structure. The local positioning system 30 and the NDE instrument 32 can be connected to a controller 42 by means of respective electrical cables 44 and 46. Although not shown in FIG. 4, an electronics box can be placed underneath the pan-tilt mechanism that has a combined cable coming out of it for all of the controllable LPS components, including the pan-tilt mechanism 38, the video camera 52 and, optionally, a laser range meter. In that case, the video camera would be connected to the electronics box via one electrical cable and then connected to the controller via the aforementioned combined cable coming out of the electronics box.

The controller 42 may comprise one or more processors that execute control functions (including controlling a camera 52 and a laser pointer 54 of the local positioning system 30, controlling the NDE instrument 32 and controlling the pan-tilt mechanism 38) and/or perform image processing (such as detecting and locating an anomaly and measuring the size and/or depth of the anomaly). The laser pointer 54 produces an eye-safe laser beam 56. A laptop PC 50 provides a user interface for configuring and inputting commands to the controller 42 and viewing acquired imaging data and calculation results on its display screen.

Figure 5:
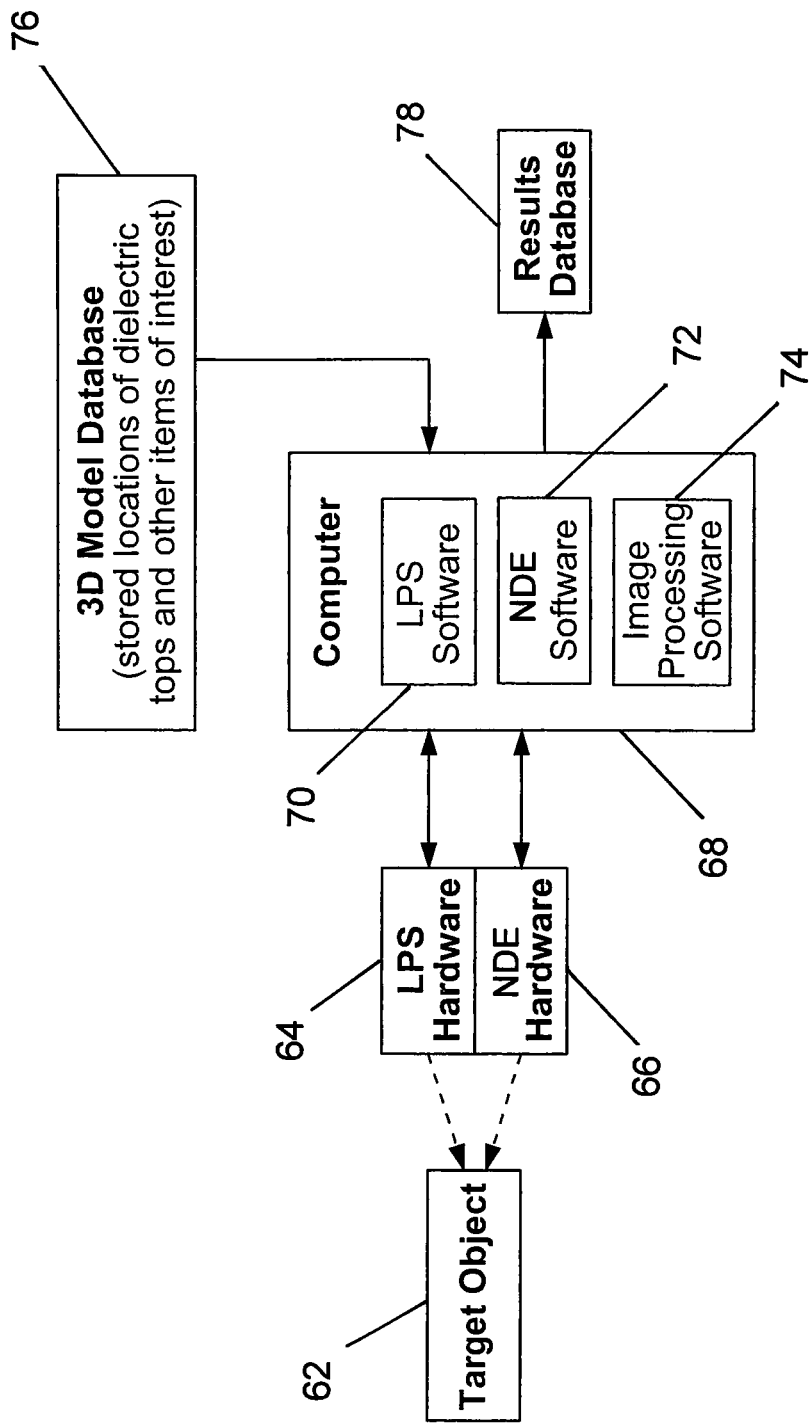
FIG. 5 is a block diagram showing the architecture of a system for stand-off inspection of aircraft structures.

FIG. 5 shows an architecture of one system for stand-off inspection of a target object 62. This system comprises a computer 68 which is coupled to local positioning system (LPS) hardware 64 and to nondestructive evaluation (NDE) hardware 66. The computer 68 is programmed to execute operations in accordance with software modules stored in computer memory. Such software modules may include LPS software 70, NDE software 72 and image processing software 74. The LPS software 70 controls the LPS hardware; and calibrates the LPS unit to the airplane coordinates, determines the direction vector to the target, and captures the visual images of the target. The image processing software 74 locates anomalies (e.g., cracks) within the image, measures their length and determines the location to direct the LPS to aim the NDE instrument for NDE measurement data acquisition. The NDE software 72 controls the NDE hardware 66 and acquires the NDE measurement data (note that the NDE images are derived from the NDE measurement data) and determines the depth of the crack. During inspection, the computer 68 may retrieve coordinate positions of features on the surface of the target object (such as dielectric tops or other items of interest) from a three-dimensional model database 76 that stores feature positions.

The data associated with LPS positioning will be referred to herein as "position measurement data". The data associated with the visible image captured by the LPS camera will be referred to herein as "imaging data". The data associated with the NDE system will be referred to herein as "NDE measurement data". The position measurement data, imaging data and NDE measurement data may be stored in a results database 78.

Although FIG. 5 shows a single computer, the software modules may be hosted by respective computers or processors of a computer system. Such a computer system may have two or more computers or processors that communicate through a network or bus.

Figure 6:
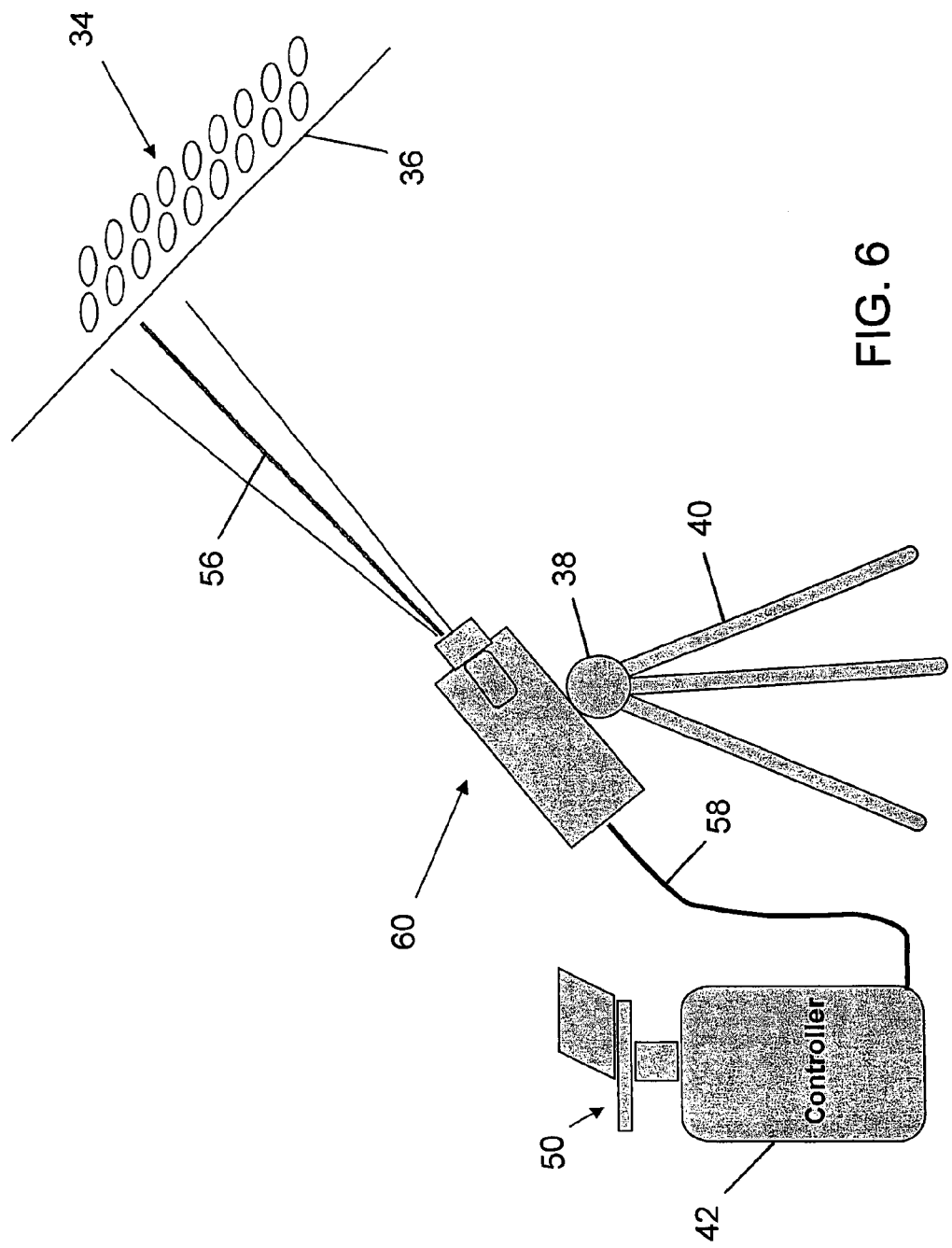
FIG. 6 is a diagram showing a system for stand-off inspection of an array of dielectric tops on an aircraft wing in accordance with another embodiment wherein the local positioning system and the NDE instrument are an integrated unit.

FIG. 6 shows an alternative embodiment in which the local positioning system and the NDE instrument are integrated in a single unit 60. Integrated unit 60 is connected to the controller 42 via an electrical cable 58. The pan-tilt mechanism 38 can be controlled via the same cable. A mirrored mechanism (disposed inside the integrated unit 60 and not visible in FIG. 6) rotates in front of the pointing laser to provide alignment; then is moved out of the way for NDE sensing to take place. In alternate embodiments, instead of a moving mirror, the camera may be moved in and out of the alignment path.

Although FIGS. 4-6 depict systems for stand-off detection and measurement of cracks in dielectric tops 34 disposed on an aircraft wing 36, other aircraft components can also be inspected using the techniques disclosed herein. More generally, the disclosed techniques have application in any situation where stand-off inspection of a structure is called for.

Figure 7:
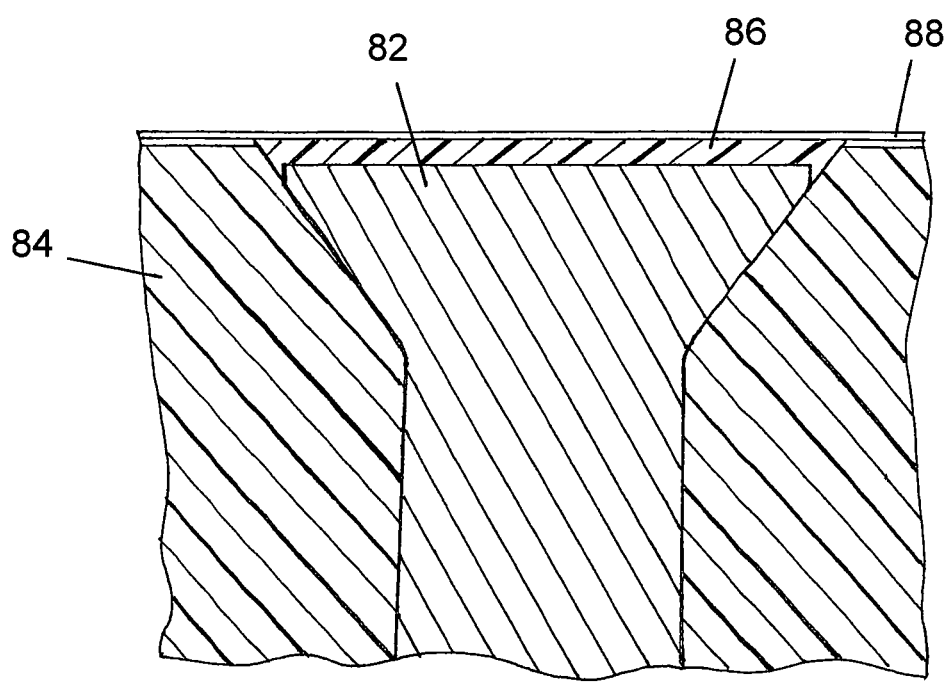
FIG. 7 is a diagram showing a cross-sectional view of the upper portion of a fastener on an aircraft wing that has been covered by a patch made of dielectric material to provide lightning protection.

FIG. 7 is a sectional view of a portion of a fastener joint in which a fastener 82 that fastens two parts of an aircraft wing (only wing surface component or skin 84 is shown) is covered by a patch 86 made of dielectric material (e.g., Kapton™ manufactured by the E. I. Du Pont de Nemours and Company). Patch 86 covers the head of fastener 82 to prevent lightning strikes from penetrating the part 84 and entering the fuel tank area. The wing surface component or skin 84 may be made of composite material covered by a layer of paint 88.

It is known that dielectric tops (i.e., patch 86 in FIG. 7) are susceptible to cracking after a certain number of years in service. An operator of aircraft so equipped (or a third-party maintenance service provider) can locate fasteners that have dielectric tops and identify cracked dielectric tops in an accurate and fast manner, and then measure the depth of those cracks in an accurate and fast manner. Cracks above a certain length may require repair or replacement of the dielectric tops.

Figure 8:
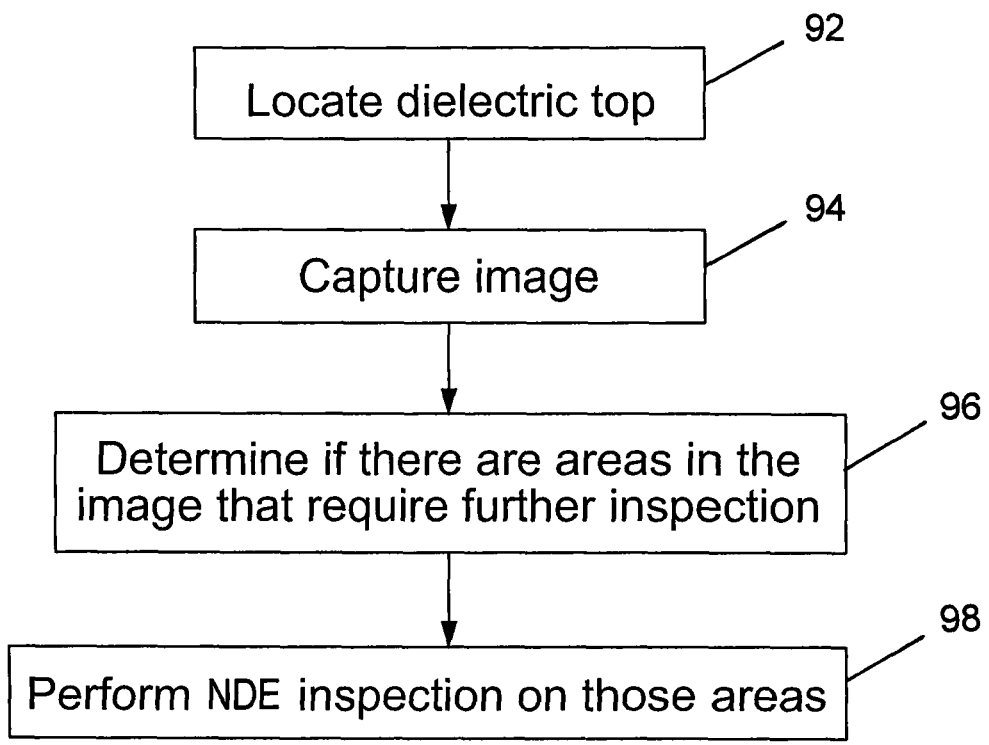
FIG. 8 is a flowchart showing phases of a process for system for stand-off inspection of an array of dielectric tops on an aircraft wing

The flowchart of FIG. 8 shows the standoff inspection process at a high level. After the LPS has been calibrated with respect to the coordinate system of an aircraft wing, a dielectric top on the wing is located (step 92) by instructing LPS to aim at a specific location representing the position of a dielectric top. An image of the located dielectric top is then captured (step 94). Steps 92 and 94 are repeated for all dielectric tops that call for inspection. A computer system processes the position measurement data and the imaging data acquired during steps 92 and 94 to determine if there are areas in the image that call for NDE inspection (step 96). The NDE instrument is then employed to inspect those areas (step 98).

Prior to automated determination of the conditions that trigger the NDE inspection, the definition of what counts as an anomaly is supplied by an expert/inspector. If the NDE expert defines a long thin region as an item to be flagged for further inspection, such a region may be a crack or a scratch or a stray mark from a permanent marker. For all such cases, the system will record the location of the anomaly in the image. From the imaging data alone, the system cannot determine whether the detected anomaly is a crack. NDE measurement data is used to make the latter determination. The data collection method depicted in FIG. 8 significantly reduces the burden on the inspector for finding the dielectric tops that call for further inspection by filtering out all areas which do not meet the previously specified criteria for the minimum level of potential damage.

Figure 9:
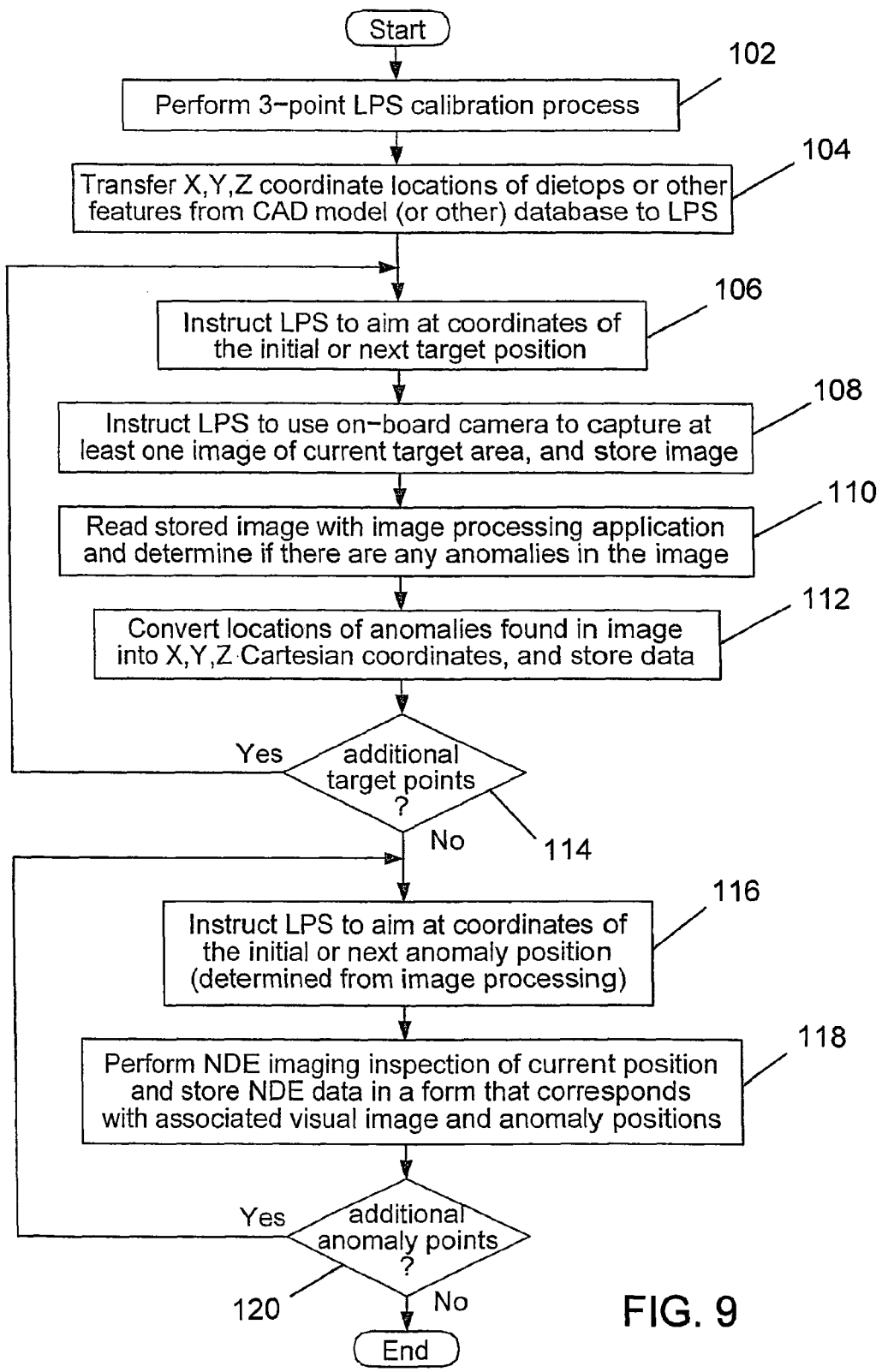
FIG. 9 is a flowchart showing various steps of a standoff NDE process in accordance with one embodiment.

A method for dielectric top inspection in accordance with one embodiment, using the system depicted in FIG. 4 is shown in FIG. 9. In step 102, the LPS is calibrated on a region of the wing (or other part of the aircraft) by measuring the positions of at least three known points. Then the coordinate locations of dielectric tops (or other features) to be inspected are exported from a CAD model (or other database) and transferred to the LPS (step 104). This is accomplished either through a data file or by way of a socket connection between the CAD modeling application and the LPS. The system operator then instructs the LPS to aim at the initial or next target position (step 106). For each dielectric top (or other feature) to be inspected, the high-resolution, high-zoom camera of the LPS will be aimed at the specific coordinates and will capture one or more images of the current target area (step 108). The stored image will be read using an image processing application capable of determining if there are any anomalies in the image (step 110). More specifically, image processing software will locate anomalies (i.e. differences from the nominal) in the captured image, and then measure the length, area, or other dimensions of damage on the surface depicted in the captured image. Locations of any anomalies within the analyzed image are converted into Cartesian (X,Y, Z) coordinates in the frame of reference of the airplane coordinate system and then recorded (step 112). (Step 112 in FIG. 9 may include steps 520, 522, 524, 526, 528 and 530 shown in FIG. 3.) If multiple target locations are inspected in the scan area, the image processing steps 110 and 112 may be performed in parallel with the capture of subsequent images in steps 106 and 108.

In step 114, a determination is made whether additional target points should be imaged. If Yes, then the routine returns to step 106; if No, then the system operator can instruct the LPS to aim at the initial or next anomaly position (step 116) (determined during the aforementioned image processing). The system operator then instructs the controller to activate the NDE instrument to perform NDE inspection of the current anomaly position and store the acquired NDE measurement data in a form that corresponds with the associated visual image and anomaly positions (step 118). The acquired data can be processed by the controller to determine the crack (or other damage) depth. In step 120, a determination is made whether additional anomaly points should undergo NDE inspection. If Yes, then the routine returns to step 116; if No, then the NDE inspection can be terminated. Optionally, prior to termination of the NDE inspection process, a final check can be performed on the collected data to confirm that valid data was collected for all called for locations (not shown in FIG. 9). This type of check may include: (1) checking each measured position to confirm that it matches the specified position (to address the possibility of occlusions, such as an object blocking the location from view); and (2) confirming that images of the appropriate size, zoom level, and lighting levels were captured. The data integrity status at each location may be recorded in the database.

Note that after the initial setup and calibration of the LPS instrument (step 102), the remainder of the data capture process described in FIG. 9 is automated. The NDI results collected by the system (step 118) will be analyzed by expert (human) inspectors. This method of data collection frees the inspector from the tedious and time consuming tasks of finding and collecting the raw data.

The computer system that controls the inspection process can store a digital record in computer memory (or other storage medium) that correlates image data (acquired by the video camera), NDE measurement data (acquired by the NDE instrument), location on the wing (or other structure being inspected), inspection date/set-up, etc. for all dielectric tops (or other features) that were inspected.

After an area has been scanned, an inspector may select a "locate" option, in response to which the controller is programmed to cause the LPS pan-tilt unit to move, aiming and pausing at each dielectric top (or other feature under inspection) that calls for repair or removal for a duration sufficient for an inspector to manually mark those tops for follow-up.

Any one of a plurality of stand-off NDE methods can be used to measure the depth of a crack (or other damage on the aircraft), such as near-infrared spectroscopy (using a spectrograph with lensing for distance measurement), terahertz imaging (using a terahertz camera with lensing for distance measurement), stand-off infrared thermography (using a thermal imaging camera), and laser shearography (using a shearographic measurement system. Other methods which can be integrated with a local positioning system for stand-off NDE and positioning for composite structure include laser ultrasonic testing (using lasers to generate and detect ultrasonic waves in the component under test) and laser vibrometry (using a laser scanning vibrometer). Stand-off microwave imaging or x-ray backscatter imaging could also be used for crack depth or other damage measurements.

Near-infrared spectroscopy is a spectroscopic method that uses the near-infrared region of the electromagnetic spectrum (with a wavelength of about 800 to about 2,500 nm).

In infrared thermography testing of a dielectric top, a focused imaging camera is used to detect radiation in the infrared range of the electromagnetic spectrum (from about 9,000 to about 14,000 nm) emitted by a selected dielectric top.

A terahertz camera comprises an image converter configured to receive incoming terahertz radiation on a forward face and to convert the incoming radiation to visible radiation. In one type of terahertz camera, the image converter includes a rigid base component made of a sapphire crystal, a thermochromic liquid crystal layer applied to a forward face of the rigid base, and a thermal absorption layer applied to the forward face of the liquid crystal. A visible light source may be configured to illuminate the rearward face of the converter. A detector adapted to detect visible light emitted from a rearward face of the converter is provided. The detector can capture a visible image formed on a rearward face of the thermochromic liquid crystal layer.

Laser shearography is especially useful in detecting defects which are situated below a surface and not detectable using visual inspection. The sample under test is illuminated using a laser and imaged on a CCD camera via a special optical shearing element. In laser shearography testing of a dielectric top, a surface area of a selected dielectric top is illuminated with a highly coherent laser light. A stochastical interference pattern, called a speckle, is created. This speckle can be compared to a known reference interference pattern.

In laser ultrasonic testing of a dielectric top, a laser pulse is directed onto the surface of a selected dielectric top through free space. That laser pulse interacts at the surface of the dielectric top to induce an ultrasonic pulse that propagates into the dielectric top. The ultrasonic pulse interrogates a feature of interest and then returns to the surface. A separate laser receiver detects the small displacement that is produced when the ultrasonic pulse reaches the surface using a measurement head.

A method for stand-off inspection of dielectric tops on an aircraft wing will now be described in more detail, including disclosure of additional features.

(1) The LPS is calibrated on a region of the wing by taking at least three known points and comparing that to the CAD model of the aircraft. Then, it uses the CAD model to locate all the dielectric tops (or other selected features on the aircraft) to be inspected.

(2) The LPS is programmed to scan across the wing and stop at each dielectric top, or set of (two or four) dielectric tops (or other features on the aircraft to be inspected).

(3) The LPS collects and saves narrow field-of-view (high zoom), high-resolution optical (visual) images for analysis, inspection documentation, and retrieval for maintenance tracking.

(4) Image analysis software, with feature extraction and geometric measurement capabilities, identifies and measures the crack length at the surface of the dielectric top (or other surface damage on features to be inspected).

(5) If an anomaly is found that is greater than a predetermined length (for example, 0.1 inch), the computer running the LPS triggers the standoff NDE device to collect and save an NDE image of the same dielectric top(s). This NDE image can be from a terahertz, near-infrared, infrared, laser ultrasonic testing, backscatter X-ray or other sensor/camera (see above) that is lensed to collect NDE measurement data at a distance of 5 to 20 feet.

(6) The depth of the anomaly (or information about the damage) is automatically measured using analysis software of the amplitude, phase, width, or other characteristic of the NDE signal received from each anomaly location.

(7) Dielectric tops with one or more cracks over a specified length or depth (or other inspected features with damage over a certain size) can be automatically assigned a "watch", "repair" or "removal" code that is tied to their location. For small cracks (or other damage), a repair of the dielectric top (or other aircraft feature under inspection) could be done. For larger damage, a complete removal and replacement may be needed. For example, if the measured crack length or depth is greater than a first threshold, the crack can be tagged for removal; if the measured crack length or depth is greater than a second threshold but lower than the first threshold, the crack can be tagged for repair; and if the measured crack length or depth is greater than a third threshold but lower than the second threshold, the crack can be tagged for watching.

(8) The LPS can access three-dimensional model data and coordinates of the part, so locations (in the coordinate system of the aircraft wing) of cracked dielectric tops (or other damaged features) can be specifically documented.

(9) The system triggers an alarm to indicate a crack has been found and indicates the length of the crack (using image software acting on the optical inspection data), and the depth of the crack (using the terahertz, near-infrared or other inspection method that probes beneath the surface). The position of any cracked or previously repaired dielectric tops (or other damaged features) can be quickly found using the LPS, even if the aircraft or the LPS has been moved since the time when the inspection was performed.

(10) The LPS can point an eye-safe laser beam at the cracked dielectric tops found during the scanning and imaging, so the inspector can go to the ones indicated and mark them for repair or replacement.

(11) The system can save additional inspection time by skipping dielectric tops (or other inspected features) recently validated or repaired, and going to only those that call for inspection.

(12) The repair database connected to LPS will keep a digital record (image data, NDE measurement data, location on wing, inspection date/set-up, etc.) for all tops, including tops that call for repair or removal. It will provide digital marking in a database, with easy-access visual correlation to the aircraft three-dimensional model. A representation of the flaw itself could be exported from the system for use in a three-dimensional modeling/CAD environment. This allows users to see the flaw in context with other models, and provides a three-dimensional record for future inspections.

(13) A follow-up inspection of a repair can be done as well, with the LPS pointing the NDE device only to those tops (or features) that were just repaired or replaced. If a different stand-off NDE method is called for, the LPS is simply dismounted from the previous device and mounted onto the new one, or a separate integrated system is used. A quick calibration with known points on the aircraft will then have the new device tied into the coordinate system of the aircraft.

The means and methods disclosed hereinafter for implementing the combination of local positioning with stand-off NDE is not limited in its application to detecting cracks in dielectric tops. Other aircraft components can also be inspected using the techniques disclosed herein. More generally, the disclosed techniques have application in any situation where stand-off inspection of a structure is called for.

The LPS aiming and image capture processes can run in parallel with the image processing. This is possible by designing a LPS architecture which supports distributed processing. Such a LPS unit can move, capture images, and then store the images to a mapped network drive, while a separate image processing computer (or multiple image processing computers) process the image data. In this configuration, there is no need for the system to wait at each location for the image processing to complete. By the time LPS finishes capturing the images, most of the images have already been processed to find anomalies. This also allows separate (more advanced) image processing techniques to be developed and inserted into overall system in the future. Alternatively, the image processing task can be performed on the same computer as the one controlling the other LPS functions provided that computer has sufficient processing power.

The LPS enables the stand-off NDE methods disclosed above to have the capability of directly tying into the aircraft coordinate system and determining where damage, NDE measurement data, and repairs are located. The image processing software used for finding anomalies can be tuned to detect specific types of flaws. A manual or semi-automated sensitivity adjustment control can be implemented to allow the operator or system to adjust the size of the anomalies that are found. Stand-off inspection with positioning capability will increase both speed of inspection and accuracy of inspection by doing it automatically, and can do so without a robot arm or robotic crawler, thereby reducing the costs of inspection.

For the specific dielectric top application, cracks in dielectric tops over fasteners may create a safety-of-flight issue. Obviously, the cost avoidance for the right inspection and repair methods is very large. A consistent, repeatable, accurate inspection method that identifies the cracks at a size before they become an issue is valuable from a cost as well as safety standpoint. There is a cost avoidance associated with such a method, because it extends the time between inspections relative to a method that sees larger cracks, such as a simple visual method that relies on human sight alone. A more significant cost avoidance provided by this invention is provided by the automation and speed of inspection. This invention can reduce significantly the man-hours and manpower to do a dielectric top inspection. In addition, on-aircraft inspections use support equipment such as scissor or boom lifts that can potentially damage the aircraft and human interactions that sometimes result in injuries. These costs can be avoided as well.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

As used in the claims, the term "computer system" should be construed broadly to encompass a system having at least one computer or processor, and which may have two or more computers or processors that communicate through a network or bus.

As used in the claims, the phrase "a position of the anomaly" should be construed broadly to encompass the position of an anomaly that is a single point and the position of a single point of an anomaly that comprises multiple points (e.g., an anomaly which is a crack or an area).

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A system comprising:
   a support;
   a pan-tilt mechanism mounted to said support;
   an assembly mounted to said pan-tilt mechanism, said assembly comprising a camera and a nondestructive evaluation instrument which are affixed to each other; and
   a computer system programmed to execute the following operations:
   (a) controlling said pan-tilt mechanism to determine a direction vector to a target object;
   (b) controlling said camera to acquire image data representing an image of an area on a surface of the target object which is intersected by the direction vector;
   (c) processing the image data to determine whether the image of the area includes information indicating presence of an anomaly in the area;

(d) if it is determined in operation (c) that the image data includes information indicating the presence of an anomaly in the area, determining coordinates of a position of the anomaly relative to a coordinate system of the target object based on the image data;

(e) controlling said pan-tilt mechanism to direct said nondestructive evaluation instrument toward an area on the target object having said coordinates; and (f) controlling said nondestructive evaluation instrument to acquire nondestructive evaluation measurement data from said area on the target object having said coordinates using a stand-off nondestructive evaluation technique.

2. The system as recited in claim 1, wherein said computer system is further programmed to process the nondestructive evaluation measurement data to determine a value for a first characteristic of the anomaly.

3. The system as recited in claim 2, wherein said computer system is further programmed to process the image data to determine a value for a second characteristic of the anomaly.

4. The system as recited in claim 3, wherein the anomaly is a crack, the first characteristic is a depth of the crack, and the second characteristic is a length of the crack.

5. The system as recited in claim 3, further comprising image analysis software resident in said computer system, wherein said computer is programmed to use said image analysis software to determine the position of the anomaly relative to the coordinate system of the target object and then determine the second characteristic of the anomaly.

6. The system as recited in claim 1, further comprising a laser pointer and three-dimensional localization software resident in said computer system, wherein said computer is programmed to control said laser pointer and use said three-dimensional localization software to determine a position and an orientation of said pan-tilt mechanism relative to the coordinate system of the target object based on light transmitted by said laser pointer and returned by the target object.

7. The system as recited in claim 1, wherein said nondestructive evaluation instrument is selected from the following group: a terahertz camera with lensing, a near-infrared spectrograph with lensing for distance measurement, a thermal imaging camera, microwave imaging, x-ray backscatter imaging, a shearographic measurement system, lasers to generate and detect ultrasonic waves, and a laser scanning vibrometer.

8. The system as recited in claim 6, wherein said computer system is further programmed to control said laser pointer to direct a laser beam toward said area on the target object having said recorded coordinates in response to a user input.

9. The system as recited in claim 1, wherein said computer system is further programmed to receive coordinate positions of features on the surface of the target object from a three-dimensional database of feature positions and then control said pan-tilt mechanism to move a line of sight of said camera across the surface, stopping at each of said coordinate positions of said features to acquire image data.

10. A method for stand-off inspection comprising:

(a) acquiring position measurement data representing the position of an area on a surface of a target object relative to a coordinate system of the target object using a local positioning system;

(b) rotating an assembly comprising a camera affixed to a nondestructive evaluation instrument so that the camera is directed toward the area;

(c) acquiring image data representing the area;

(d) processing the image data to determine whether the image data includes information indicating the presence of an anomaly in the area;

(e) if it is determined in step (d) that the image data includes information indicating the presence of an anomaly in the area, determining coordinates of a position of the anomaly relative to the coordinate system of the target object based on the image data;

(f) recording said coordinates of the position of the anomaly;

(g) rotating the assembly so that the nondestructive evaluation instrument is directed toward an area on the target object having said recorded coordinates; and (h) acquiring nondestructive evaluation measurement data using a stand-off nondestructive evaluation technique.

11. The method as recited in claim 10, further comprising processing the nondestructive evaluation measurement data to determine a value for a first characteristic of the anomaly.

12. The method as recited in claim 11, further comprising processing the image data to determine a value for a second characteristic of the anomaly.

13. The method as recited in claim 12, wherein the anomaly is a crack, the first characteristic is a depth of the crack, and the second characteristic is a length of the crack.

14. The method as recited in claim 12, further comprising using image analysis software to determine the position of the anomaly relative to the coordinate system of the target object and then determine the second characteristic of the anomaly.

15. The method as recited in claim 10, wherein the target object is an aircraft and the anomaly is damage to the aircraft.

16. The method as recited in claim 15, wherein the area corresponds to a location of a dielectric top on a wing of the aircraft.

17. The method as recited in claim 10, further comprising using three-dimensional localization software to determine a position and an orientation of the camera relative to the coordinate system of the target object.

18. The method as recited in claim 10, wherein said nondestructive evaluation technique is selected from the following group: near-infrared spectroscopy, terahertz imaging, stand-off infrared thermography, laser shearography, laser ultrasonic testing and laser vibrometry.

19. The method as recited in claim 10, further comprising directing a laser beam toward said area on the target object having said recorded coordinates.

20. The method as recited in claim 10, further comprising receiving coordinate positions of features on the surface of the target object from a three-dimensional database of feature positions and then rotating the assembly so that the camera scans across the surface, stopping at each of said coordinate positions of said features to acquire image data.

21. A method for detecting and determining a position of a visible anomaly on a target object, said method comprising:

(a) locating, by position and orientation, a local positioning system comprising a camera having a nondestructive evaluation instrument affixed thereto with respect to a target object;

(b) determining the position and orientation offset between the position and orientation of the local positioning system located in step (a) and a prior position and orientation of a local positioning system previously utilized to collect a set of reference images of the target object, the prior position and orientation being in the coordinate system of the target object;

(c) relocating, by position and orientation, the local positioning system with respect to the target object in accordance with the offset determined in step (b);

(d) using the camera to acquire a set of images of the target object from the position and orientation of the relocated local positioning system;

(e) comparing the set of images to corresponding images within the set of reference images to detect a difference between the acquired images and the corresponding reference images;

(f) determining coordinates of a position of the detected difference in the coordinate system of the target object based on the acquired images and the corresponding reference images;

(g) recording said coordinates of the position of the detected difference; and (h) relocating, by position and orientation, the local positioning system with respect to the target object so that nondestructive evaluation instrument is directed toward the detected difference using said recorded coordinates.

22. The method as recited in claim 21, further comprising:

(i) acquiring measurement data representing a characteristic of the detected difference using a nondestructive evaluation technique; and (j) processing the measurement data to determine a value for the characteristic of the detected difference.

23. The method as recited in claim 22, wherein comparing the set of just acquired images to corresponding reference images comprises determining a relative displacement of features common to both an acquired image and a corresponding image within the set of reference images.

24. A method for nondestructive evaluation inspection of an area on a surface of a target object using a camera and a nondestructive evaluation instrument which are affixed to each other, comprising:

determining, relative to a coordinate system associated with a target object, coordinates of a position for a visibly detectable anomaly on a surface of a target object based on image data captured by the camera;

directing the nondestructive evaluation instrument toward the visibly detectable anomaly using said recorded coordinates;

acquiring measurement data representing a characteristic of the visibly detectable anomaly using the nondestructive evaluation instrument; and processing the measurement data to determine a value for the characteristic of the visibly detectable anomaly.

25. A system for stand-off inspection comprising a video camera, a laser range meter, a nondestructive evaluation instrument, and a motion-controlled pan-tilt mechanism, said video camera, said laser range meter, and said nondestructive evaluation instrument being supported by said motion-controlled pan-tilt mechanism and fixed relative to each, and further comprising a computer system programmed to perform the following operations:

controlling said motion-controlled pan-tilt mechanism so that a line of sight of said camera is directed toward an area on a surface of the target object;

processing said image data to determine whether an anomaly is present in said area;

if an anomaly is present, determining coordinates of a position of said anomaly in a coordinate system of said target object based on said imaging data;

controlling said motion-controlled pan-tilt mechanism to direct said nondestructive evaluation instrument toward a position corresponding to said coordinates; and controlling said nondestructive evaluation instrument so that nondestructive evaluation measurement data is acquired by said nondestructive evaluation instrument while directed toward said position corresponding to said coordinates.

26. The system as recited in claim 25, wherein said computer system is further programmed to measure a characteristic of said anomaly based on said nondestructive evaluation measurement data.

* * * * *